United States Patent [19]

Blankenship et al.

[11] Patent Number: 5,116,312
[45] Date of Patent: May 26, 1992

[54] METHOD AND APPARATUS FOR AUTOMATIC AUTOTRANSFUSION

[75] Inventors: Howard B. Blankenship; Fred D. Wallace, both of Birmingham, Ala.

[73] Assignee: The UAB Research Foundation, Birmingham, Ala.

[21] Appl. No.: 431,296

[22] Filed: Nov. 3, 1989

[51] Int. Cl.⁵ .............................................. A61M 5/00
[52] U.S. Cl. ........................................ 604/66; 604/65; 604/67; 364/413.07
[58] Field of Search .................... 364/413.07; 604/4, 5, 604/6, 7, 50–53, 65–67; 128/DIG. 12, DIG. 13

[56] References Cited

U.S. PATENT DOCUMENTS

| | | | |
|---|---|---|---|
| 4,280,494 | 7/1981 | Cosgrove, Jr. et al. | 128/213 |
| 4,392,849 | 7/1983 | Petre et al. | 604/66 |
| 4,464,172 | 8/1984 | Lichtenstein | 604/65 |
| 4,710,164 | 12/1987 | Levin et al. | 604/66 |
| 4,756,706 | 7/1988 | Kerns et al. | 604/66 |
| 4,778,450 | 10/1988 | Kamen | 604/65 |
| 4,889,528 | 12/1989 | Nadai et al. | 604/65 |
| 4,946,439 | 8/1990 | Eggers | 604/67 |

Primary Examiner—Jerry Smith
Assistant Examiner—Russell Cass
Attorney, Agent, or Firm—Needle & Rosenberg

[57] ABSTRACT

A method and system for closed-loop, automated, closed, autotransfusion having a computer in electronic communication with a bedside monitor, an infusion pump, wherein the infusion pump is controlled by the computer, a blood collection canister for receiving shed mediastinal blood from a patient, means for filtering the blood, means for transferring the blood from the canister to the infusion pump and then into the patient, means for automatically taking a set of time-spaced measurements of a hemodynamic variable of the patient wherein the hemodynamic variable is coded into a multiplicity of digitally coded signals that are transmitted to the computer, and programming means for analysis of the digitally coded signals to determine the rate of the infusion pump, wherein the blood is infused at a high rate intermittently.

35 Claims, 7 Drawing Sheets

METHOD AND APPARATUS FOR AUTOMATIC AUTOTRANSFUSION

BACKGROUND OF THE INVENTION

The present invention relates to a system and method for use in the autotransfusion of blood. More particularly, the invention relates to an improved closed autotransfusion system which is automatically regulated by closed-loop feedback of relevant patient hemodynamic variables.

Autotransfusion involves the reinfusion of a patient's own blood as opposed to the transfusion of bank blood. Although intraoperative and postoperative blood conservation techniques have decreased the use of bank blood for cardiac surgical patients, the increasing number of surgical procedures has placed a strain on the bank blood supply. One procedure to reduce this strain is postoperative autotransfusion, the return of blood shed from the mediastinum or thoracic cavity following surgery. The efficacy and safety of postoperative autotransfusion has been documented (Johnson et al. *Ann Thorac. Surg.* 1983; 36:178). Furthermore, autotransfusion is the safest form of transfusion therapy because there is no risk of alloimmunization, hepatitis, acquired immunodeficiency syndrome (AIDS), or other complications possible with bank blood.

An autotransfusion system in which shed mediastinal blood is filtered and collected in a transfusion bag located within a canister is described in Schaff et al., *J. Thorac. Cardiovasc. Surg.* 1978; 75:632. When the volume of blood in the transfusion bag is adequate for reinfusion, the bag is removed from the canister, compressed to remove any air from the bag, and attached to a blood administration set. Blood collected within the bag is utilized for autologous blood infusion only if 400 ml or more is collected within a four hour period. This system, however, is inconvenient to use, costly, and has the potential for bacterial contamination. Furthermore, this system reinfuses autologous blood after approximately a four hour delay and thus does not respond quickly to hemodynamic instability caused by blood loss.

Cosgrove et al., *Ann. Thorac. Surg.* 1985; 40:519, describes a closed autotransfusion system in which the cardiotomy reservoir used during surgery is reconfigured to serve as a receptacle for postoperative mediastinal drainage. Blood drains through a chest tube and collects in the bottom of the cardiotomy reservoir after being filtered and then is reinfused using a standard infusion pump. Every hour, mediastinal drainage is measured and the infusion pump is manually adjusted to deliver this amount of blood during the next hour. Because this system reinfuses blood after an hour delay, the system does not allow immediate adjustment of the rate of infusion in response to patient hemodynamic instability nor does the system allow for immediate reinfusion of shed blood. Furthermore, the system requires that the nursing staff manually perform routine maintenance every hour the system is operational.

Cardiac index (heart rate times stroke volume per square meter of body surface area) is known to be an important indicator for predicting survival and recovery in the postsurgical cardiac patient. Heart rate can be paced postsurgically when necessary for optimal cardiac index but convenient methods for reliable, repetitive measurements of stroke volume in the clinical environment do not yet exist. However, the left atrial pressure (LAP) correlates with the stroke index (stroke volume per square meter) and thus is one of the determinants of stroke volume. Infusion of blood increases LAP and thus infusion can be used to affect a patient's hemodynamic stability. However, when LAP exceeds 12-15 mm Hg in most adult patients, the cardiac index no longer rises. Thus, 12-15 mm Hg is an optimal mean LAP for most adult patients.

Sheppard et al., *Ann. Surg.* 1968; 168:596 and Sheppard et al., *Fed. Proc.* 1974; 33:2327 utilize this concept in their cardiac surgical intensive care computer system. This system provides for the infusion of banked blood using closed-loop feedback based upon a combination of the patient's left atrial pressure (LAP) and the total blood infused-to-total blood drained ratio. A constant rate 20 ml dose of blood is automatically infused every two minutes so long as neither the LAP nor the total blood infused-to-drained ratio exceeds a preset limit; if these limits are exceeded, no blood is infused. Although this bank blood system attempts to stabilize a patient's hemodynamic characteristics by infusing blood to raise a patient's LAP, this system is incapable of responding minute-by-minute to a patient's blood loss; blood loss is measured only to prevent overinfusion. Furthermore, in the event of a computer-to-pump communication failure or a general computer failure during infusion, the system continues to infuse bank blood at a constant rate regardless of the patient's LAP or total blood infused-to-blood drained ratio. No provision is made to keep a patient's vein open during periods that either the LAP or the total blood infused-to-drained values exceed their limits. Also, the LAP and chest drainage measurements are susceptible to infusion-related distortions and the patient does not receive the benefits inherent with autologous blood.

Therefore, there exists a need for a fully-automated, closed, closed-loop autotransfusion system that employs an adjustable infusion rate to maintain a patient's total blood volume and respond minute-by-minute to a patient's hemodynamic instability. As used herein, the term "closed system" refers to a system that is protected from bacterial contamination; the term "closed-loop system" refers to a system in which the imput or excitation to the system is automatically changed to produce a desired output.

SUMMARY OF THE INVENTION

The present invention relates to a method and system for closed, closed-loop, automated autotransfusion. This system includes a computer that is in electronic communication with a bedside monitor and bedside keyboard to provide a bedside display of and control over the course of the autotransfusion. A blood collection canister collects blood as it drains from the patient's mediastinum or thoracic cavity; this blood, which is appropriately filtered, is then transferred to a variable rate infusion pump for immediate reinfusion into the patient. Hemodynamic variables, such as the patient's right or left atrial pressure or the weight of the blood within the blood collection canister, are measured and signals corresponding to these measurements are sent to the computer for analysis. The rate of reinfusion, which is adjusted by the computer as frequently as every minute, varies depending upon the current amount of blood in the blood collection canister, the value of a patient hemodynamic variable such as the LAP, and the possibility of inaccurate physical measurements. If conditions are suitable, an aliquot of blood is infused at a high rate followed by a period of at least 10 seconds in which no blood is infused. Otherwise, a low rate of infusion is set by the computer to keep the patient's vein open unless an error is detected, in which case no infusion occurs.

Multiple bedside units can be networked using one computer to create a larger system. Optionally, the system can include additional pumps to infuse other circulatory supportive fluids whose administration is also regulated with appropriate patient vital-sign feedback. The computer maintains an up-to-the minute record of all measurements and documents the course of treatment.

Accordingly, one objective of this invention is to provide a closed, closed-loop automatic autotransfusion system in which the rate of reinfusion is based upon the current status of the patient's hemodynamic variables. This system provides for the immediate return of shed mediastinal blood to the patient. In addition, this system promotes hemodynamic stability by adjusting infusion rates based on the patient's minute-by-minute bleeding rates, keeping hemodynamic instability secondary to blood loss at a minimum. A further objective of this invention is to keep the patient's circulating blood volume essentially constant. A still further objective of this invention is to promote hemodynamic stability by automatically adjusting the infusion rate of autologous blood based upon time-spaced measurements of the patient's hemodynamic variables. Furthermore, this invention provides for an automated autotransfusion system that, once initiated, requires minimal human supervision or intervention.

In addition, it is an object of this invention to provide for an autotransfusion system in which a variable rate of reinfusion is employed depending on whether the hemodynamic variables indicate that it is appropriate to infuse at a high rate to promote hemodynamic stability, at a low rate to ensure that the patient's vein remains open or no infusion if an irregularity in the system is detected. Furthermore, it is an object of this invention to provide for high-rate, intermittent autotransfusion in which the computer signals the infusion pump to infuse a small volume of blood at a high-rate followed by a period of time during which no infusion occurs. This high-rate, intermittent autotransfusion promotes safety in a computer-operated system by ensuring that no infusion takes place if there is a computer-to-pump communication failure or a general computer failure. Furthermore, this high-rate, intermittent autotransfusion provides a period of time between a high-rate infusion of an aliquot of blood and the sampling of atrial pressures to ensure that pressure transients from the infusion do not distort the measurements. This time period also allows any electronic transients to damp out in the blood drainage measurement system and thus allows for an undistorted measurement of the blood in the blood drainage canister. These and other objects and advantages of the present invention are apparent to a person skilled in the art from the following detailed description.

DETAILED DESCRIPTION OF THE INVENTION

Figure 1:
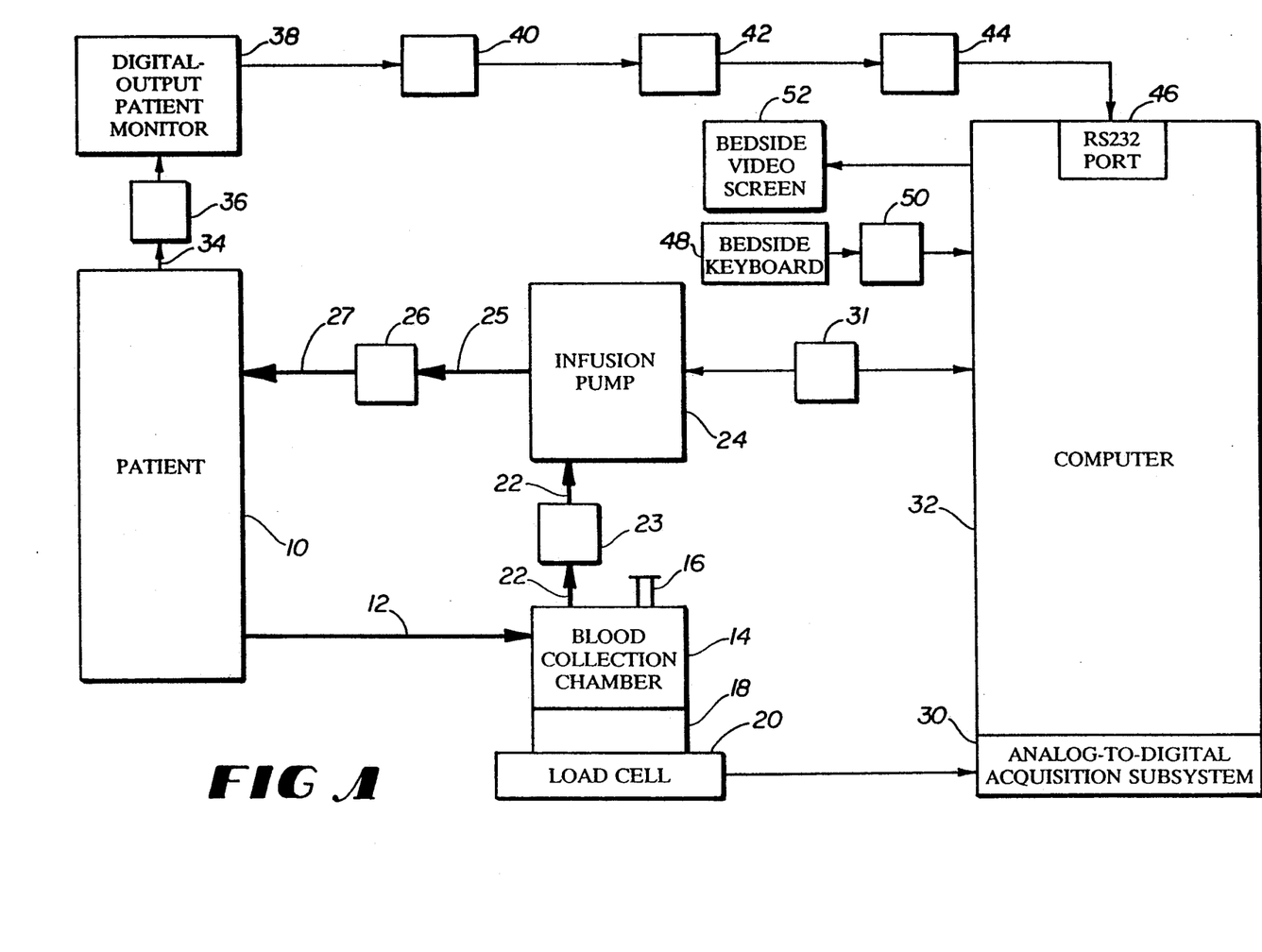
FIG. 1 shows a block diagram of a preferred embodiment of the present invention for a closed, closed-loop, automatic autotransfusion system.

The preferred embodiments of the present invention are now described with reference to the drawings, wherein like parts are designated with like numerals throughout. More particularly, FIG. 1 shows a first embodiment of the present invention. This system for the automatic autotransfusion of autologous blood into a patient broadly includes a blood collection chamber 14, an infusion pump 24, a pressure transducer 36 for measuring the right or left atrial pressure of a patient 10, a load cell 20 for measuring the weight of blood collection chamber 14, a computer 32, a bedside video display screen 52, and a bedside keyboard 48.

Shed mediastinal blood drains from the patient 10 through chest drainage tubes 12 into the blood collection chamber 14, which is preferably a cardiotomy reservoir converted for use as a receptacle for postoperative mediastinal drainage as disclosed in Cosgrove et al., *Ann Thorac. Surg.* 1985; 40:519. Optionally, the blood collection chamber 14 is equipped with a 20 μm pore size filter for removing clots from the blood. The blood collection chamber 14 is connected to a vacuum source 16, preferably −15 to −25 cm H$_2$O pressure. The blood collection chamber 14 is also attached to conduit 22, preferably intravenous tubing, suitable for transporting the autologous blood from the blood collection chamber 14 to an infusion pump 24, preferably a high-rate volumetric infusion pump such as IMED model number 980C. Optionally, conduit 22 is attached an to in-line 20 μm pore size blood filter 23 to remove blood clots. The infusion pump 24 is in flow communication with conduit 22 and conduit 25, preferably intravenous tubing, which delivers the blood to an in-line 20 μm pore size blood filter 26. The filtered blood exits filter 26 and enters conduit 27, preferably an intravenous blood administration set, which is connected to a vein of patient 10, preferably a peripheral vein. The path that the shed mediastinal blood travels from the patient 10 through chest tubes 12 to the blood collection chamber 14, to the infusion pump 24, and back into the patient 10 is maintained as a closed system so that the blood is protected from bacterial contamination.

The weight of the blood collection chamber 14 is measured and converted to a voltage proportional to the weight of chamber 14 by load cell 20, preferably a Gould Statham UTC3 load cell with mechanical attenuator 18 or AL Design Inc. ALD-DLC-51b load cell. Load cell 20 generates an analog signal corresponding to weight of the blood collection chamber 14. This signal is transmitted, via intervening circuitry, to the analog-to-digital acquisition subsystem 30 of computer 32.

A pressure line 34 is attached to patient 10 to measure the left or right atrial pressure of patient 10. This pressure line 34 is attached to a pressure transducer 36, which generates an analog signal corresponding to the left or right atrial pressure. This signal is transmitted, via intervening circuitry, to a digital-output patient monitor 38. The monitor 38 provides a digital signal which is transmitted, via network control 40, microcomputer 42, communication buffer 44, and intervening circuitry, to RS232 port 46 of computer 32.

The computer 32, preferably a minicomputer such as Hewlett-Packard 21MXE, uses the data acquired in the analog-to-digital acquisition subsystem 30 and through the RS232 port 46 to calculate the rate of infusion for pump 24 as described in greater detail below. The computer 32 transmits a signal, via a point-to-point topology addressing scheme in code operated switch 31 and intervening circuitry, to pump 14 to control the rate of infusion of blood. A bedside keyboard 48 is electronically connected to computer 32 via keyboard controller/multiplexer 50 and intervening circuitry to allow bedside control of computer 32. Bedside video screen 52, which is connected to computer 32 via intervening circuitry, allows for the visual display of parameters associated with the automatic autotransfusion system.

Figure 2:
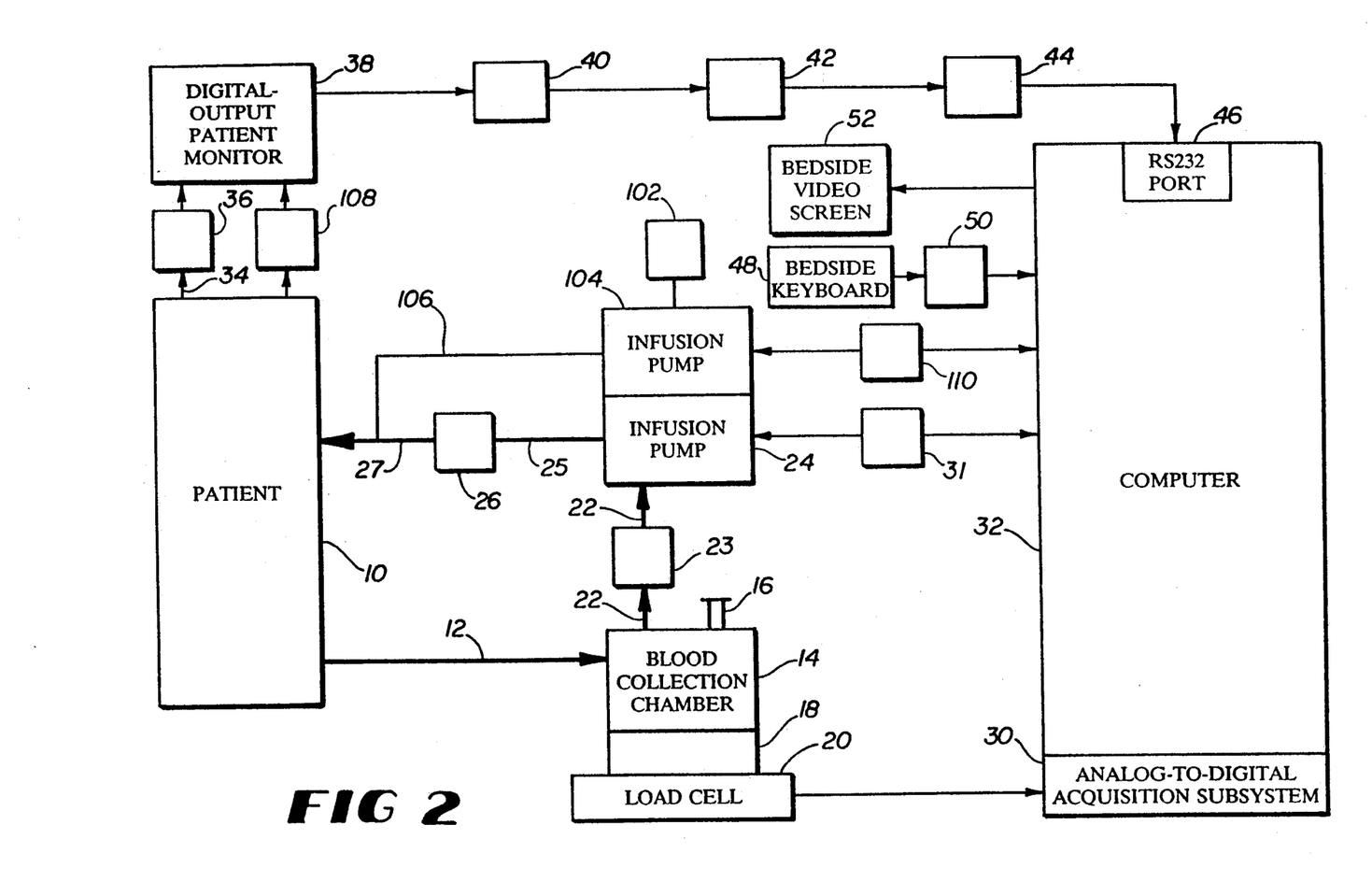
FIG. 2 shows a block diagram for a second embodiment of the present invention for a closed, closed-loop, automatic autotransfusion system.

FIG. 2 shows a second embodiment of the present invention similar to the previous embodiment shown in FIG. 1 except for the addition of a second infusion system to infuse a biocompatible fluid into patient 10 for circulatory support. A reservoir 102, containing a biological fluid, such as washed autologous blood, bank blood products such as whole blood, packed cells, or plasma, or a solution containing albumin, hetastarch, or a drug, is connected to a second infusion pump 104, preferably a high-rate volumetric infusion pump such as IMED model number 980C. The infusion pump 104 is linked to conduit 106, preferably intravenous tubing, which in is connected to conduit 27, preferably an intravenous blood administration set to deliver the biological fluid into a vein, preferably a peripheral vein, of patient 10.

A physiological variable, such as heart rate or left atrial pressure, is measured by transducer 108 or, if the physiological variable is identical to that measured to regulate autotransfusion as described above, transducer 36, which generates an analog signal corresponding to the physiological variable. This signal is transmitted, via intervening circuitry, to digital-output patient monitor 38. The monitor 38 provides a digital signal which is transmitted, via network controller 40, microcomputer 42, communications buffer 44, and intervening circuitry, to RS232 port 46 of computer 32. The computer 32, using the data received from the RS232 port 46, calculates the rate of infusion for pump 104. The computer 32 transmits a signal, via a point-to-point topology addressing scheme in code operated switch 110 and intervening circuitry, to pump 104 to control the rate of infusion of the biological fluid. It can be appreciated by one skilled in the art that infusion pumps 24 and 104 could be replaced by a multichannel infusion pump.

Figure 3:
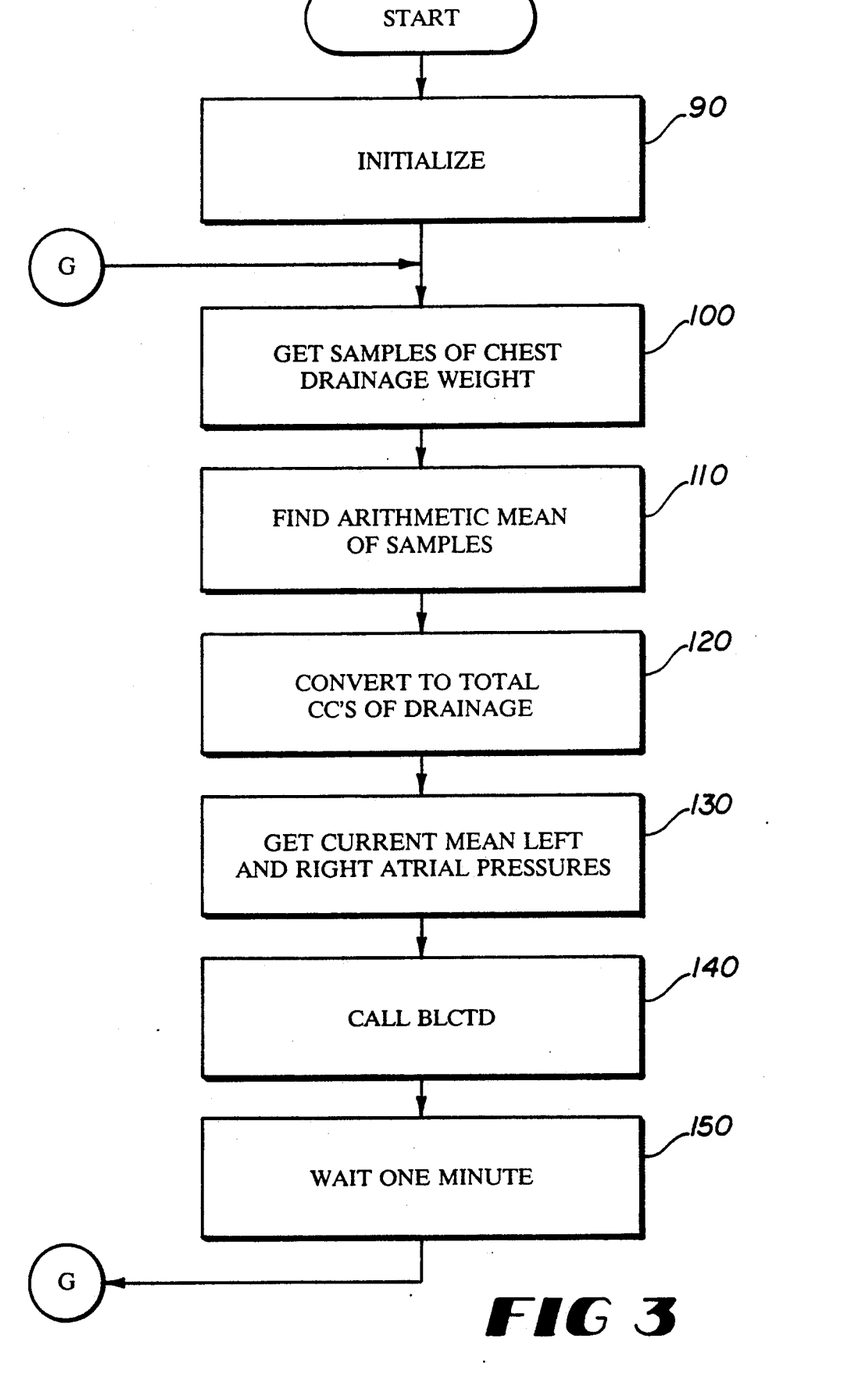
FIG. 3 is a schematic flow chart depicting the data processing methodology for controlling the closed, closed-loop, automatic autotransfusion system in accordance with the present invention.

The basic steps for determining the rate of infusion in accordance with the present invention can be understood with reference to FIG. 3. Functional block 90 sets default values or values selected from the bedside keyboard 48 for the following parameters: (1) choice of measuring LAP or RAP (default=LAP); (2) volume to infuse (default=20 ml for adult>50 Kg); (3) infusion rate (default=1499 ml/hr; 20 ml in 48 sec.); (4) LAP or RAP limit (default=14); (5) time for total autotransfusion period (default=10 hr.); (6) residual blood drainage maintained in blood collection chamber 14 (default=150 cc.) and (7) interval between successive infusion cycles (default=1 min.). The volume to infuse is preferably selected based upon the weight of the patient; the rate of infusion is designed to allow at least a 10 second interval during which no blood is infused to allow measurement of the blood collection chamber 14 and LAP or RAP without infusion-related distortion.

As shown in functional block 100, a number of weights, preferably 6, each 1 second apart, of the blood collection chamber 14 are acquired from the computer A/D measurement subsystem. Functional blocks 110 and 120 represent the process in which the arithmetic mean of the samples are converted to cubic centimeters of thoracic drainage. Current values for patient variables, including mean left and mean right atrial pressure, are acquired and placed in the patient data base as shown in block 130. The routine for controlling autotransfusion actuation is called from functional block 140. The main process repeats every minute.

Figure 4A:
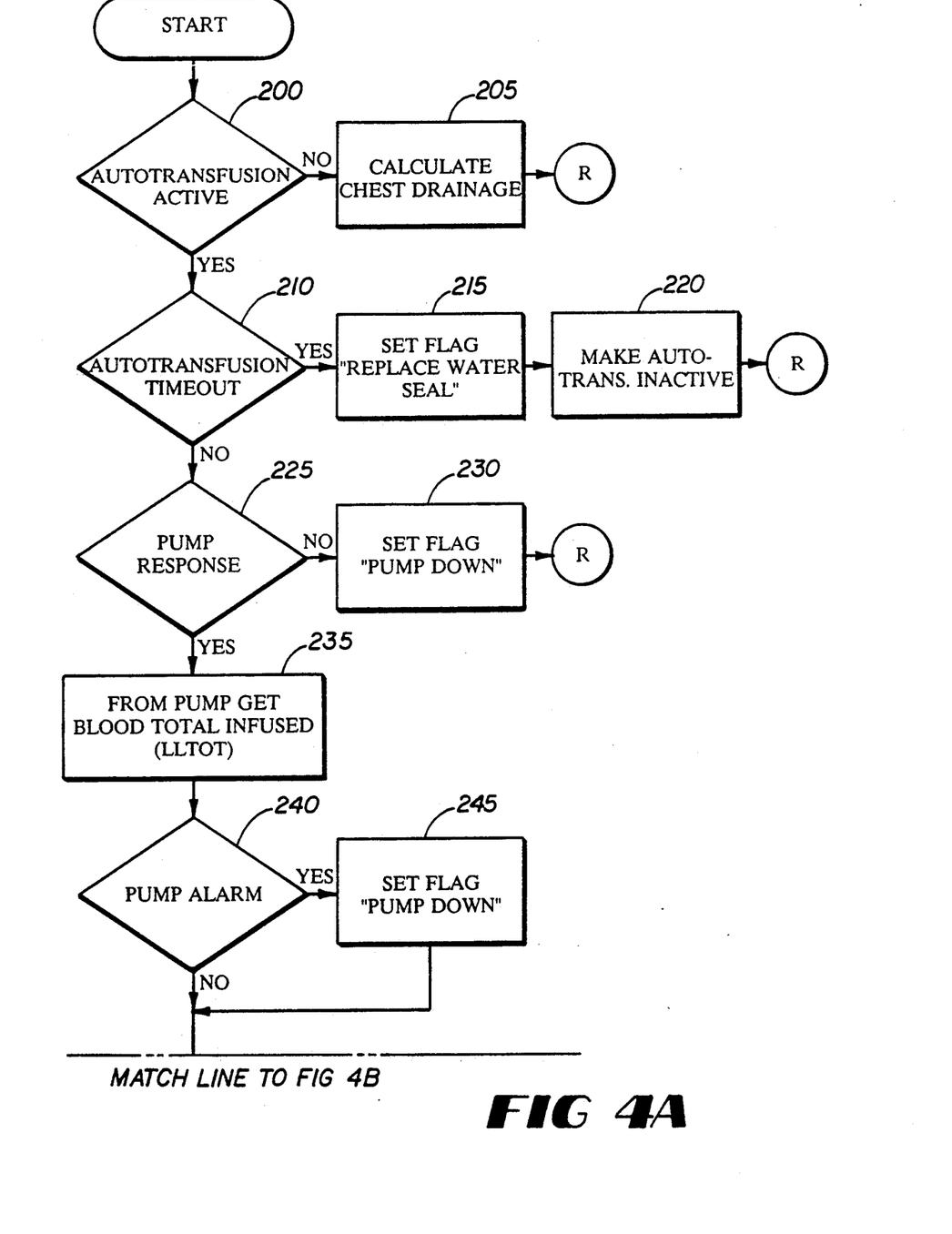
FIGS. 4a through c is a schematic flow chart depicting the routine for controlling autotransfusion actuation.
Figure 4B:
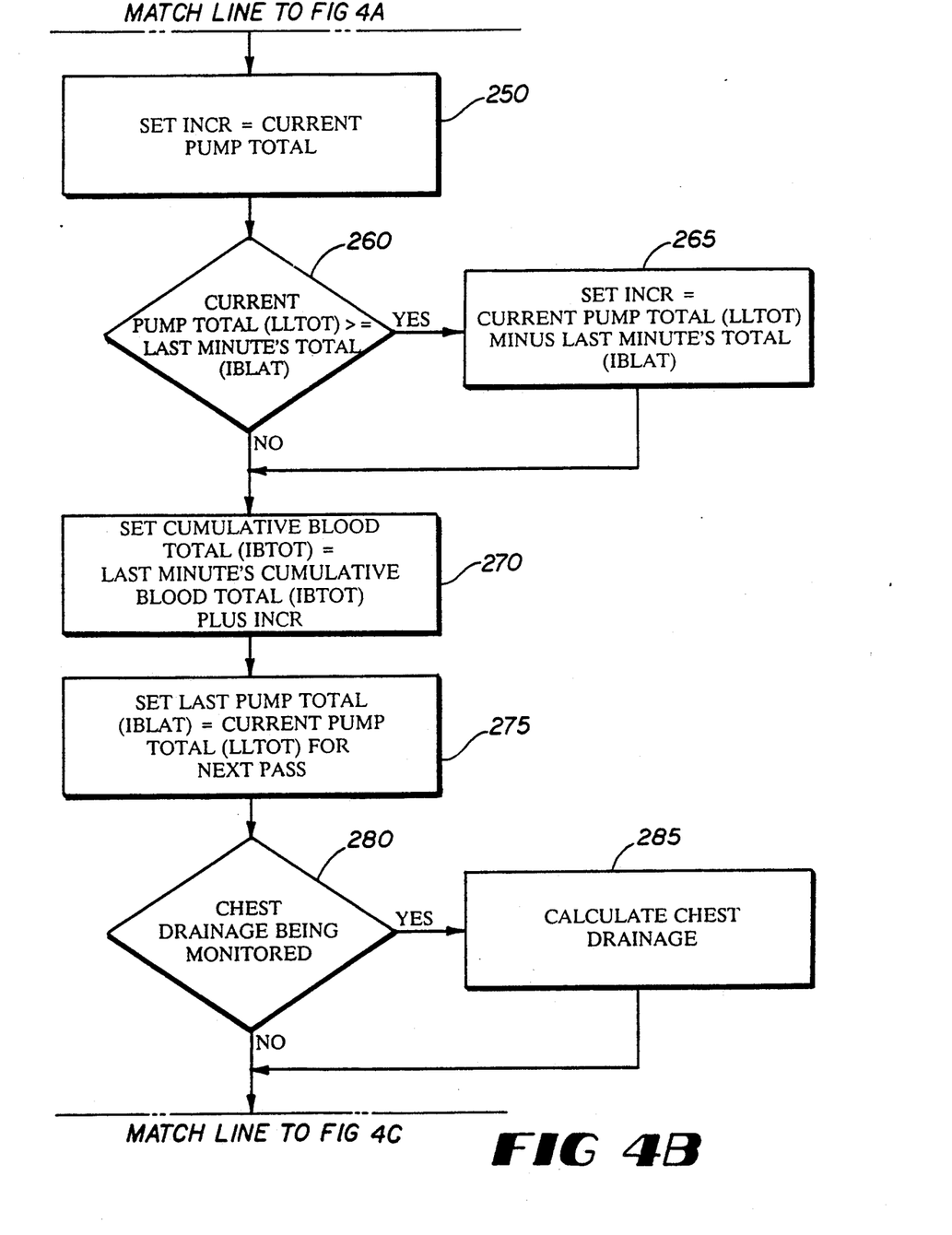
Figure 4C:
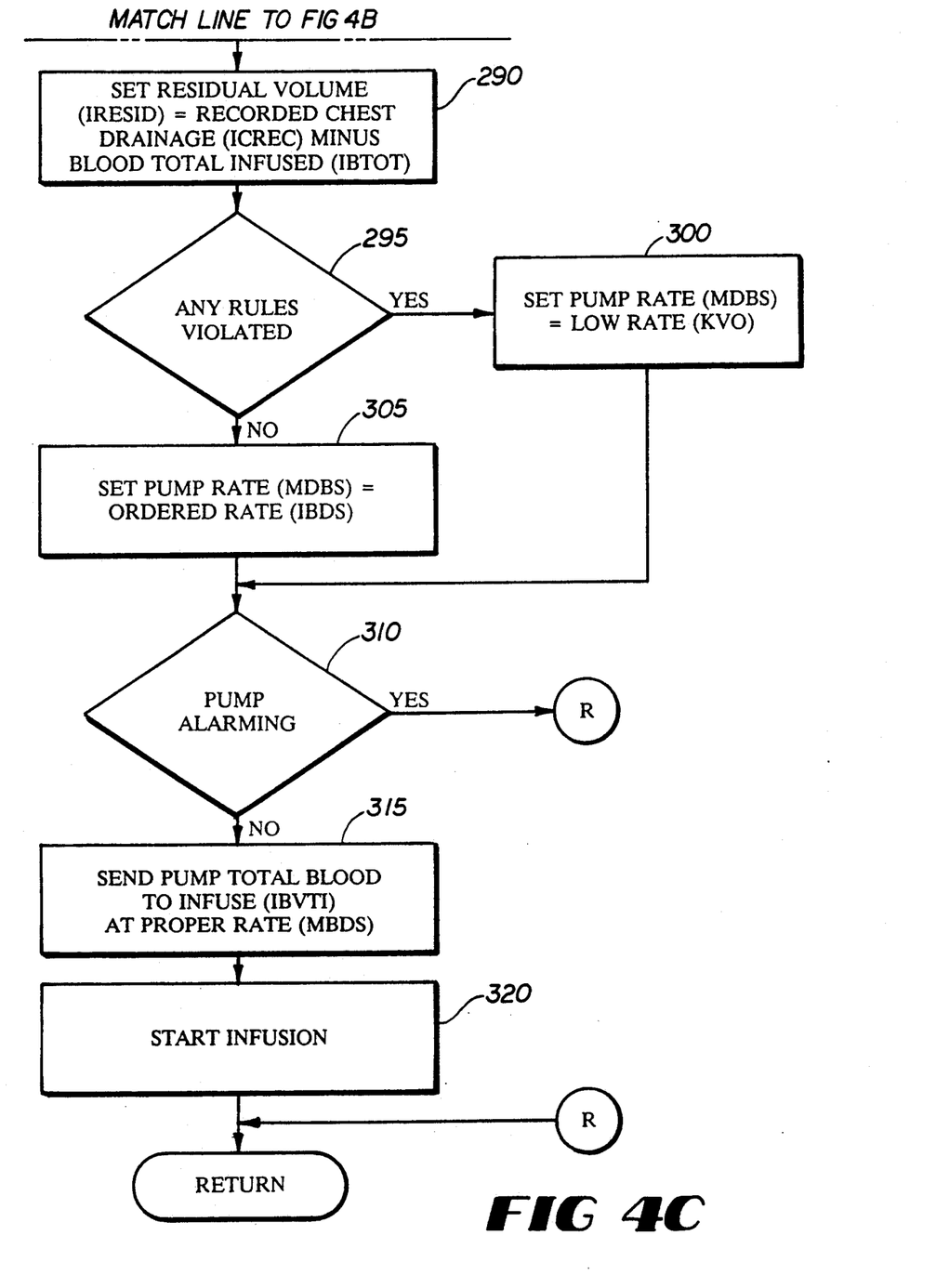

FIG. 4 describes the routine for controlling autotransfusion actuation. A check is first made in functional block 200 to determine if the autotransfusion process is active. If not, only the chest drainage calculations are done and control is returned to the main program. If the autotransfusion process has timed out, a flag is set to send a message to the bedside video screen for the user to create a water seal, which is used as a diagnostic aid to detect air leaks when autotransfusion is not used, and the process is made inactive, as shown in blocks 215 and 220. If the infusion pump is responding to computer polls, the total volume of blood that the pump has infused is acquired in functional block 235. A temporary variable (INCR) is set equal to the total that the pump has infused (LLTOT) in block 250. If the pump total has been reset due to user intervention during the intervening minute, INCR will remain the same as the pump total (LLTOT), but under normal circumstances the variable INCR will become the difference between LLTOT and the total from the last minute (IBLAT); this is shown in blocks 260 and 265. The cumulative blood total (IBTOT) then becomes last minute's cumulative total plus INCR in block 270.

Chest drainage is calculated for the autotransfusion system in block 285 if chest drainage monitoring is enabled. In either case, the residual volume (IRESID), which is the volume of blood that should be visible in the drainage canister and the intravenous tubing, is set to the difference between the recorded chest drainage (ICREC) and the total blood infused (IBTOT), as shown in block 290.

Functional blocks 295, 300, and 305 are the important elements in determining the rate that is sent to the infusion pump. The pump rate is set to the high-rate default or the rate that has been entered from the bedside keyboard if all the rules apply for giving a high-rate aliquot. The pump rate is set to a low rate to keep the vein open if any of the rules are violated. The rules are: (1) The autotransfusion is not under one-minute control or under two-minute control and it is not at the two-minute mark; (2) There is sufficient drainage in the blood collection chamber 14 to give the ordered aliquot and maintain the ordered residual volume; (3) A feedback variable is the left atrial pressure, the LAP is above the set limit, and the LAP and chest drainage monitoring is not enabled; (4) A feedback variable is the right atrial pressure, the RAP is above the set limit, and the RAP and chest drainage monitoring is not enabled; and (5) A recent measurement for the chest drainage volume is beyond reasonable limits.

After the pump is sent a rate and a volume to infuse in blocks 315 and 320, control is returned to the main program.

Figure 5:
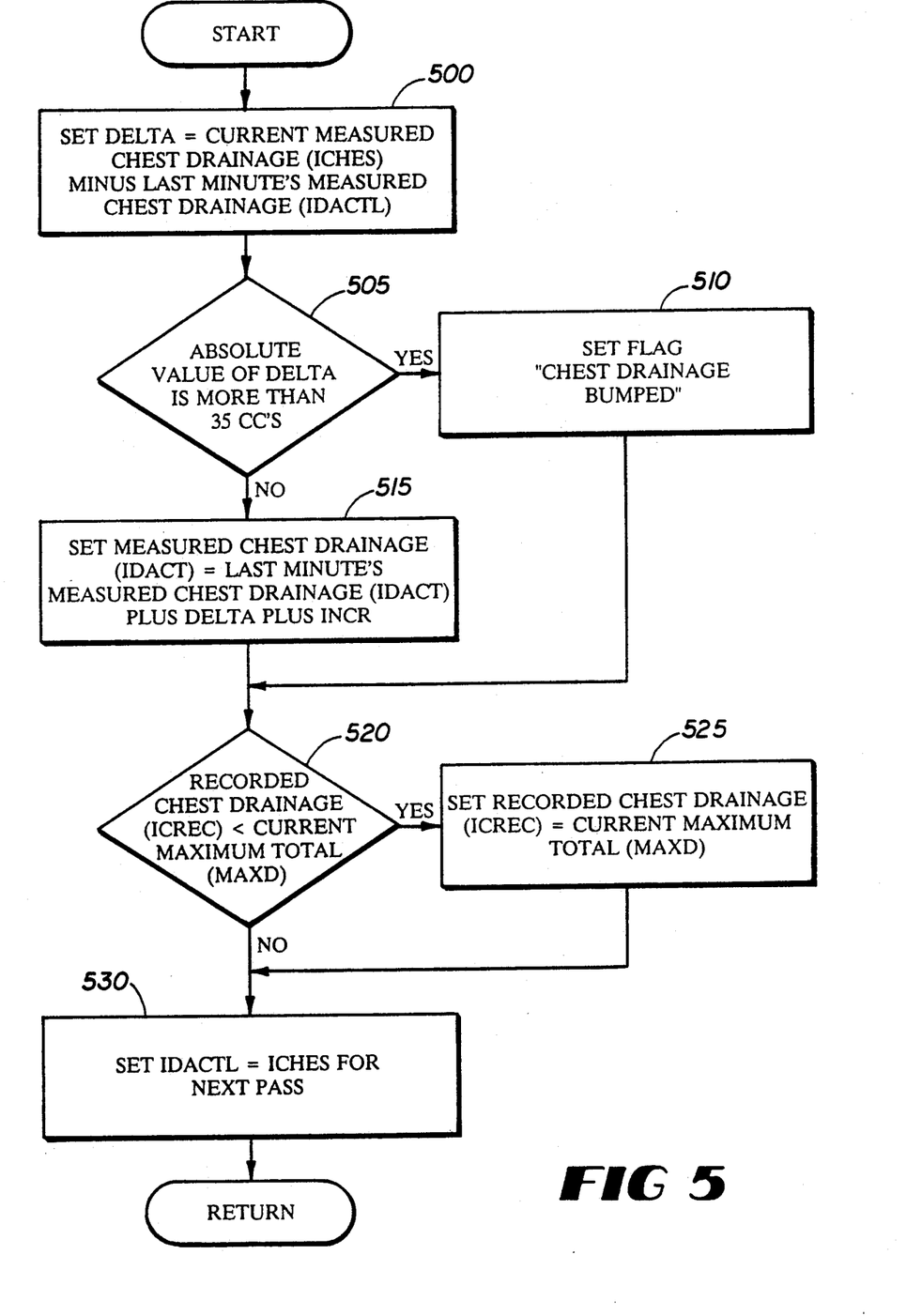
FIG. 5 is a schematic flow chart depicting the routine for determining the volume of shed mediastinal blood.

The routine for calculating chest drainage in functional blocks 285 and 205 must take into account cases when autotransfusion is active and also when autotransfusion is inactive so that the blood collection chamber 14 functions as a normal chest drainage receptacle. The procedure for this is shown in FIG. 5.

First, a temporary variable (DELTA) is calculated as the current averaged chest drainage measurement (ICHES) minus last minute's measured chest drainage (IDACTL), as shown in functional block 500. The value DELTA represents the total of the drainage that has entered the blood collection chamber 14 during the last minute less the volume of blood that has been pumped from the canister during the last minute. Blocks 505, 510, and 515 show the manner in which the chest drainage measurement is incremented. If the value of DELTA is found to be outside of a predetermined reasonable limit, such as 35 cc's, the chest drainage total is not modified, and a flag is set to place a message on the video screen that the measurement is questionable. Otherwise, the measured chest drainage (IDACT) is calculated as the sum of last minute's measured chest drainage plus DELTA plus INCR. A separate value for recorded chest drainage (ICREC) is maintained that remains unchanged or increases each minute. The exact measurement, IDACT, may have small variations that could be slightly negative with respect to the previous minute's value; therefore, since the chest drainage total can only increase, the exact measurement is kept internal to the computer and not displayed. The recorded chest drainage is changed only when the exact measurement exceeds the recorded value, as seen in blocks 520 and 525.

Thus, this invention can be used following cardiac surgery to automatically reinfuse shed mediastinal blood. The cardiotomy reservoir that is used during surgery can be converted to an autotransfusion blood collection chamber 14 and connected to the patient's chest tubes 12. Normally, the cardiotomy reservoir is already equipped with a "sock" filter of 20 μm pore size for removing clots; the filtered blood needs no anticoagulant prior to reinfusion due to is defibrinogenation. Sterility is maintained in the closed system, and blood can be pumped from the bottom of the blood collection chamber 14 as fresh drainage enters the top.

The blood collection chamber 14 is transported with the patient from the operating room to the intensive care unit following surgery, placed on a chest drainage measurement stand, and connected to wall suction with $H_2O$ regulation. A voltage proportional to the weight of the blood collection chamber is sent to computer 32 and subsequent changes in the blood collection chamber 14 weight are converted to incremental volumes of shed mediastinal blood.

When sufficient drainage in the blood collection canister 14 is noted by nursing personnel, the autotransfusion procedure is begun. Conduit 23 is connected from the bottom of the blood collection chamber 14 to infusion pump 24. Autotransfusion is started by sending a signal to computer 32 from bedside keyboard 48 after entering desired parameters unless default parameters are acceptable. Entries may include the maximum acceptable left atrial pressure level and the volume of blood to maintain in blood collection chamber 14. A residual volume of blood is kept in chamber 14 to avoid draining all available blood and having to restart the procedure.

Computer 32 returns an aliquot of blood (usually 20 ml for adults) to the patient during each minute provided that (1) the left atrial pressure is within the selective limit; (2) there is sufficient drainage in the chamber 14; and (3) the measured value for the drainage during the latest minute is within reasonable limits. If any of these rules are violated, the pump 24 is sent a low infusion rate for keeping the patient's vein open. An air embolism detector (not shown) integral to the pump 24 halts any pumping action if air is sensed in the intravenous line. Personnel are alerted to pump alarms or questionable measurement values by messages on bedside video screen 52. The computer 32 maintains an up-to-the-minute record of the total drainage, rate of drainage, and the amount of blood that has been reinfused along with other stored parameters.

In order to avoid bacterial contamination of the blood, the computer 32 normally ends the procedure after 10 hours by turning off the infusion pump 24 and displaying a message on bedside video monitor 52. The intravenous tubing is removed from the system, and the blood collection chamber 14 is thereafter used as a normal thoracic drainage receptacle. In rare instances, a new sterile cardiotomy reservoir is set up, and the computer 32 timer is reset for a additional 10-hour period.

Appendix

```

      IMPLICIT INTEGER(A-Z)
      DEFINE(KVO,10)              #KVO RATE OF 10 ML PER HOUR
      DEFINE(LAFEED,1)            #LAP FEEDBACK SELECT
      DEFINE(RAFEED,2)            #RAP FEEDBACK SELECT
      DIMENSION IVAL(19),^        #MEMORY RESIDENT MAILBOXES
                IDCB(144),^       #READ/WRITE BUFFER FOR DISK
                NAMQ(3),^         #FOR FILE NAME
                IBLOD(25),^       #BLOOD FILE PORTION OF BED FILE
                IFCA(2),^         #TEMPORARY STORAGE
                NAMB(20)          #BEDFILE NAMES

      EQUIVALENCE(IBDS,IBLOD(3)),(IBTOT,IBLOD(5)),(IBVTI,IBLOD(6)),^
                 (IBLAT,IBLOD(7)),(IMED,IBLOD(8)),(LUBLD,IBLOD(9)),^
                 (LIMLA,IBLOD(16)),^
                 (IRES,IBLOD(18)),(I1TWO,IBLOD(20)),(IDACT,IBLOD(21)),^
                 (MAXD,IBLOD(22)),(IQUIT,IBLOD(23)),(IQCNT,IBLOD(24)),^
                 (ISEL,IBLOD(25)),(IVAL(13),IDACTL),(IVAL(7),ICREC)

      DATA NAMB/2H01,2H02,2H03,2H04,2H05,2H06,2H07,2H08,2H09,2H10,2H11,2H12,^
               2H13,2H14,2H15,2H16,2H17,2H18,2H19,2H20/

# SUBROUTINE PARAMETERS:

#     NBD IS THE BED NUMBER
#     KT2 IS THE DATA DESCRIPTOR FOR EVEN OR ODD MINUTE (1=ODD,2=EVEN)
#     IVAL IS THE FILE POINTER FOR MEMORY RESIDENT MAILBOXES
#     MOU17 IS THE DATA WORD FOR SYSTEM MESSAGES
#     ICHES IS THE CURRENT RAW CHEST DRAINAGE MEASUREMENT
#     ITIM IS THE SYSTEM TIME OF DAY

# BLOOD FILE VARIABLES:

#     IBDS IS THE ORDERED RATE OF INFUSION
#     IBTOT IS THE BLOOD TOTAL INFUSED
#     IBVTI IS THE BLOOD VOLUME TO INFUSE EACH MINUTE (OR EACH 2 MINS.)
#     IBLAT IS THE TOTAL READ FROM PUMP AT LAST MINUTE
#     IMED IS FLAG INDICATING WHETHER IMED BLOOD PUMP BEING USED
#     LUBLD IS THE BLOOD PUMP LOGICAL UNIT
#     LIMLA IS THE ORDERED LAP LIMIT (OR RAP LIMIT)
#     IRES IS THE SPECIFIED RESIDUAL VOLUME TO MAINTAIN
#     I1TWO IS NUMBER INDICATING 1 OR 2 MINUTE CONTROL
#     IDACT IS THE EXACT MEASUREMENT OF CHEST DRAINAGE

SUBROUTINE BLCTD(NBD,KT2,IVAL,MOU17,ICHES,ITIM)

#     MAXD IS THE CURRENT MAXIMUM MEASURED CHEST DRAINAGE
#     IQUIT IS TIME FOR AUTOTRANSFUSION TO SHUT ITSELF OFF
#     IQCNT IS THE BACKUP TIMER (INTERVAL COUNTER)
#     ISEL IS FEEDBACK SELECT (1=LAP, 2=RAP)

#     IDACTL IS THE EXACT CHEST DRAINAGE MEASUREMENT
#     ICREC IS THE RECORDED CHEST DRAINAGE MEASUREMENT

      NAMQ(1) = 2HKF
      NAMQ(2) = 2H07
      NAMQ(3) = NAMB(NBD)
      IERR = UOPEN(IDCB,NAMQ,1)
      IERR = UREAD(IDCB,2,33,IBLOD,25)
      IERR = UCLOS(IDCB)
      IQCNT=IQCNT-1                #DECREMENT INTERVAL COUNTER
      IBTOT = IVAL(18)
      LAP = IVAL(6)
      RAP = IVAL(5)
      INCA = IVAL(15)

```

```
       IF(IMED==1 & MOU17<0)    #ELSE JUST DO CHEST CALCULATIONS
          [IF(IABS(ITIM-IQUIT) >5  # CHECK IF AUTOTRANS HAS TIMED OUT
             & IQCNT > 0)
               [IOPTN = 1
                LUARY = LUBLD
                NOLU = 1
                CALL LURQ(IOPTN,LUARY,NOLU)   #LOCK BLOOD CARD LU
                NNBD=NBD          #FOR NOW, BLOOD ADDRESS=BED NUMBER

#   SELECT CHANNEL
           CALL PRDWD(3,0,NNBD,IPST,LUBLD,IRN,IXERR)
# GET PUMP TOTAL INFUSED SINCE LAST MINUTE
           IF(IPST==0)
               CALL PRDWD(1,2,LLTOT,IPST,LUBLD,IRN,IXERR)
# IF THE PUMP IS DOWN, DO NOT ADDRESS AGAIN
#      (SIMPLY TRY AGAIN NEXT MINUTE)
           IF(IPST==0)         #.NE. ZERO MEANS ERROR
# READ THE PUMP STATUS
              [CALL PRDWD(1,4,MVAL,IPST,LUBLD,IRN,IXERR)
# IF STATUS BITS FOR AIR-IN-LINE, OCCLUSION, OR PUMP MALFUNCTION
#      ARE ON, SET ALARM FLAG
               IF(IAND(MVAL,122B) <> 0)
                   ALARM=1
               ELSE
                   ALARM=0
ICPLT = MVAL & 4     #INFUSION COMPLETE?
               INCR = LLTOT
               IF(INCR < 0)
                   INCR = 0
               IF(LLTOT .GE. IBLAT)
                   INCR=LLTOT-IBLAT
               IBTOT=IBTOT+INCR
               IBLAT = LLTOT
               IF(IAND(INCA,128) <> 0)    #CHEST ON STATUS?
                  [DELTA =ICHES-IDACTL)   #IF SO, DO C.D. ARITHMETIC
                   IF(IABS(DELTA ). > 35)  #TOO BIG A JUMP,
                       MOU17=IOR(MOU17,16)  #SET C.D. BUMPED MESSAGE
                   ELSE
                      [IDACT=IDACT+DELTA +INCR
                       ICREC=IDACT
                       IF(ICREC < MAXD)
                                   ICREC=MAXD
                       MAXD=ICREC
                       IDACTL=ICHES
                       ]
                   ]
               IRESID=ICREC-IBTOT    #FOR LATER IN ROUTINE
               IF((I1TWO<>1 & KT2<>2)   #NOT 1 MIN. CONTROL AND NOT
                                        # 2 MIN. CONTROL NOW
               !  IRESID < (IRES+IBVTI)
               !  ((ISEL==LAFEED & (LAP>LIMLA ! IAND(INCA,244B)<>244B)))
               !  ((ISEL==RAFEED & (RAP>LIMLA ! IAND(INCA,224B)<>224B)))
               !  IAND(MOU17,16) == 16)
                       MBDS=KVO              # KVO RATE
               ELSE MBDS=IBDS        # ELSE ORDERED RATE

                         # CHECK ALARM STATUS
               IF(ALARM==1)         # PUMP DOWN
                   MOU17=IOR(MOU17,1024)
               ELSE
                  [IRATE=MBDS
              # SEND VOLUME TO INFUSE, NOT CONTINUOUS, AT PROPER RATE
                   CALL PRDWD(2,2,IBVTI,IPST,LUBLD,IRN,IXERR)
                   CALL PRDWD(2,4,111B,IPST,LUBLD,IRN,IXERR)
                   CALL PRDWD(2,1,IRATE,IPST,LUBLD,1,IXERR)
```

```
                    ]
              # ELSE PUMP NOT RESPONDING
          ELSE
                  MOU17=IOR(MOU17,1024)

#    RELEASE THE LU
              IOPTN=0
              CALL LURQ(IOPTN,LUARY,NOLU)
              ]
          # ELSE AUTOTRANS HAS TIMED OUT
          ELSE
              [MOU17=IAND(MOU17,77777B)
               INCA=IAND(INCA,047777B)              # TURN OFF AUTOTRANS BIT,
               MOU17=IOR(MOU17,40000B)              # BLOOD BITS, IN MEMORY
               IERR=UOPEN(IDCB,NAMQ,2)              # RESIDENT AND BLOOD FILES

SUBROUTINE BLCTD(NBD,KT2,IVAL,MOU17,ICHES,ITIM)

IERR=UREAD(IDCB,1,28,IFCA,2)         # AND SET BIT TO CREATE
               IFCA(1)=IAND(IFCA(1),77777B)         # WATER SEAL
               IFCA(2)=IAND(IFCA(2),047777B)
               IFCA(1)=IOR(IFCA(1),40000B)
               IERR=UWRIT(IDCB,1,28,IFCA,2)
               IERR=UCLOS(IDCB)
               ]

]

    # ELSE DO ONLY CHEST DRAINAGE CALCULATION
ELSE
      IF(IAND(INCA,128) <> 0)         # C.D. ON STATUS?
          [DELTA.=ICHES-IDACTL
           IF(IABS(DELTA ) < 35)
              [DELTA.=IDACT+IDELC
               ICREC=IDACT
               IF(ICREC < MAXD)
                              ICREC=MAXD
               MAXD=ICREC
               IDACTL=ICHES
               ]
          ELSE
                  MOU17=IOR(MOU17,16)     # SET CHEST DRAINAGE BUMPED
          ]
IF(IMED==1 & MOU17>=0)   # TRUE IF SYSTEM HAS BEEN REBOOTED AFTER CRASH
      [INCA=IAND(INCA,047777B)   # ...SO WE NEED TO TURN OFF AUTOTRANS
       IMED=0
      ]
IVAL(15)=INCA
IVAL(18)=IBTOT
IERR=UOPEN(IDCB,NAMQ,2)
IERR=UWRIT(IDCB,2,33,IBLOD,25)
IERR=UCLOS(IDCB)
RETURN
END
$
```

What is claimed is:

1. A system for closed-loop, automated, closed autotransfusion, comprising:
   (a) a computer;
   (b) a first infusion pump having a first variable infusion rate that is controlled by said computer;
   (c) a blood collection chamber;
   (d) first conduit means for transferring shed mediastinal blood from a patient to said chamber;
   (e) second conduit means for transferring said blood from said chamber to said first infusion pump;
   (f) third conduit means for transferring said blood from said first infusion pump into a view of said patient, said first conduit means, said chamber, said second conduit means, and said third conduit means defining a path of travel;
   (g) means for filtering said blood located along said path of travel;
   (h) means for collecting first data relating to a hemodynamic variable of said patient over a period of time;
   (i) means for encoding said first data into a plurality of first digitally coded signals;
   (j) means for transmitting said first digitally coded signals to said computer;
   (k) means in said computer for analyzing said first digitally coded signals to set said first rate of said first infusion pump, wherein said first rate is set for a preselected period of time and wherein said analyzing means comprise:
      (i) means for storing the value for said hemodynamic variable in the memory of said computer;
      (ii) means for determining if said infusion pump is an alarm state;
      (iii) means for ascertaining the incremental volume of said blood pumped through said first infusion pump during said preselected period of time;
      (iv) means for calculating the total volume of said blood infused by summing the respective said ascertained incremental volumes;
      (v) means for computing the volume of said blood in said chamber;
      (vi) means for calculating the volume difference in said chamber between said computed volume in said chamber and the volume of said blood in said chamber after the previous said preselected period of time;
      (vii) means for computing the incremental volume of blood drainage from the mediastinum during said preselected period to time by summing said volume difference and said ascertained volume of blood pumped through said first infusion pump;
      (viii) means for calculating the total amount of blood drainage from the mediastinum by summing said computed incremental volumes over a predetermined interval of time;
      (ix) means for setting said first infusion rate at a predetermined low rate to keep said patient's vein open upon the occurrence of a selected one of the following conditions:
         (A) if the volume of said blood in said chamber is less than a predetermined acceptable volume;
         (B) if said value for said hemodynamic variable does not fall within a predetermined acceptable range;
         (C) if said volume of blood drainage from the mediastinum during said preselected period of time exceeds a predetermined acceptable value;
      (x) means for setting said first infusion rate to deliver an aliquot of said blood at a predetermined acceptable rate unless said predetermined low rate was set in step (9); and
      (xi) means for allowing the infusion of said blood at said first infusion rate unless said first pump is in said alarm state;
   (l) a video display monitor in electronic communication with said computer for visually displaying information relating to said analyzing means; and
   (m) a keyboard in electronic communication with said computer for providing bedside control of said system.

2. The system of claim 1, further comprising:
   (a) a second infusion pump having a second variable infusion rate that is controlled by said computer;
   (b) a reservoir containing a biocompatible fluid;
   (c) fourth conduit means for transferring said biocompatible fluid from said reservoir to said second infusion pump;
   (d) fifth conduit means for transferring said biocompatible fluid from said second infusion pump into the vein of said patient;
   (e) means for collecting second data relating to a physiological variable of said patient over a period of time;
   (f) means for encoding said second data into a plurality of second digitally coded signals;
   (g) means for transmitting said second digitally coded signals to said computer; and
   (h) means in said computer for analyzing said second digitally coded signals to set said second rate of said second infusion pump for a predetermined period of time.

3. The system of claim 2, wherein said biocompatible fluid is washed autologous blood.

4. The system of claim 1, wherein said first infusion pump is a volumetric infusion pump.

5. The system of claim 1, wherein said blood collection chamber is a cardiotomy reservoir.

6. The system of claim 1, wherein said hemodynamic variable is the right atrial pressure.

7. The system of claim 1, wherein said hemodynamic variable is the left atrial pressure.

8. The system of claim 1, wherein said first data provides the volume of said blood in said chamber at a particular time.

9. The system of claim 1, wherein said first data provides the volume of said blood pumped through said first infusion pump during said preselected period of time.

10. The system of claim 1, wherein said first rate of said first infusion pump is set by said computer through a point-to-point topology pump addressing scheme.

11. The system of claim 1, wherein said first infusion pump infuses a volume of said blood followed by a period of time during which said blood is not infused by said first infusion pump to allow the collecting of said first data without infusion-related distortion during said period of time.

12. A method of closed-loop, automated, closed autotransfusion, comprising the steps of:
   (a) providing a closed autotransfusion system comprising:
      (i) a first infusion pump having a first variable infusion rate;
      (ii) a blood collection chamber;
      (iii) first conduit means for transferring shed mediastinal blood from a patient to said chamber;
      (iv) second conduit means for transferring said blood from said chamber to said first infusion pump;
      (v) third conduit means for transferring said blood from said first infusion pump into the vein of said patient, said first conduit means, said chamber, said second conduit means, and said third conduit means defining a path of travel; and
      (vi) means for filtering said blood located along said path of travel;
   (b) automating said closed autotransfusion system by integrating a closed-loop regulatory system with said closed autotransfusion system, wherein said closed-loop regulatory system comprises:
      (i) a computer, wherein said computer control said first infusion pump;
      (ii) means for collecting first data relating to a hemodynamic variable of said patient over a period of time;
      (iii) means for encoding said first data into a plurality of first digitally coded signals;
      (iv) means for transmitting said first digitally coded signals to said computer;
      (v) means in said computer for analyzing said first digitally coded signals to set said first rate of said first infusion pump, wherein said first rate is set for a preselected period of time and wherein said analyzing means comprise:
         (A) repeating steps (B) through (L) at the end of successive periods of time, wherein said time period is the said preselected period of time over which said first rate is set, until a predetermined interval of time has elapsed;
         (B) storing the value for said hemodynamic variable in the memory of said computer;
         (C) determining if said infusion pump is in an alarm state;
         (D) ascertaining the incremental volume of said blood pumped through said first infusion pump during said preselected period of time;
         (E) calculating the total volume of said blood infused by summing the respective said ascertained incremental volumes;
         (F) computing the volume of said blood in said chamber;
         (G) calculating the volume difference in said chamber between said computed volume in said chamber and the volume of said blood in said chamber after the previous said preselected period of time;
         (H) computing the incremental volume of blood drainage from the mediastinum during said preselected period to time by summing said volume difference and said ascertained volume of blood pumped through said first infusion pump;
         (I) calculating the total amount of blood drainage from the mediastinum by summing said computed incremental volumes over a predetermined interval of time;
         (J) setting said first infusion rate at a predetermined low rate to keep said patient's vein open upon the occurrence of a selected one of the following conditions:
            (i) if the volume of said blood in said chamber is less than a predetermined acceptable volume;
            (ii) if said value for said hemodynamic variable does not fall within a predetermined acceptable range;
            (iii) if said volume of blood drainage from the mediastinum during said preselected period of time exceeds a predetermined acceptable value;
         (K) setting said first infusion rate to deliver an aliquot of said blood at a predetermined acceptable rate unless said predetermined low rate was set in step (J); and
         (L) allowing the infusion of said blood at said first infusion rate unless aid first pump is in said alarm state;
      (vi) a monitor in electronic communication with said computer for visually displaying information relating to said analyzing means; and
      (vii) a keyboard in electronic communication with said computer for providing bedside control of said system.

13. The method of claim 12, further comprising the steps
   (a) providing a secondary infusion system to infuse a circulatory supportive fluid comprising:
      (i) a second infusion pump having a second variable infusion rate that is controlled by said computer;
      (ii) a reservoir containing a biocompatible fluid;
      (iii) fourth conduit means for transferring said biocompatible fluid from said reservoir to said second infusion pump; and
      (iv) fifth conduit means for transferring said biocompatible fluid from said second infusion pump into the vein of said patient.
   (b) automating said secondary infusion system by integrating a second closed-loop regulatory system with said secondary infusion system, wherein said second closed-loop regulatory system comprises:
      (i) means for collecting second data relating to a physiological variable of said patient over a period of time;
      (ii) means for encoding said second data into a plurality of second digitally coded signals;
      (iii) means for transmitting said second digitally coded signals to said computer; and
      (iv) means in said computer for analyzing said second digitally coded signals to set said second rate of said second infusing pump for a predetermined period of time.

14. The method of claim 13, wherein said biocompatible fluid is washed autologous blood.

15. The method of claim 12, wherein said first infusion pump is a volumetric infusion pump.

16. The method of claim 12, wherein said blood collection chamber is a cardiotomy reservoir.

17. The method of claim 12, wherein said hemodynamic variable is the right atrial pressure.

18. The method of claim 12, wherein said hemodynamic variable is the left atrial pressure.

19. The method of claim 12, wherein said first data provides the volume of said blood in said chamber at a particular time.

20. The method of claim 12, wherein said first data provides the volume of said blood pumped through said first infusion pump during said preselected period of time.

21. The method of claim 12, wherein said first rate of said first infusion pump is set by said computer through a point-to-point topology pump addressing scheme.

22. The method of claim 12, wherein said first infusion pump infuses a volume of said blood followed by a period of time during which said blood is not infused by said first infusion pump to allow the collecting of said first data without infusion-related distortion during said period of time.

23. The method of claim 12, wherein said preselected period of time is one minute.

24. A method for closed-loop, automated, closed autotransfusion by means of a computer, a first infusion pump having a first variable infusion rate that is controlled by said computer, a blood collection chamber, first conduit means for transferring shed mediastinal blood from a patient to said chamber, second conduit means for transferring said blood from said chamber to said first infusion pump, third conduit means for transferring said blood from said first infusion pump into the vein of said patient, said first conduit means, said chamber, said second conduit means, and said third conduit means defining a path of travel, means for filtering said blood located along said path of travel, means for collecting first data relating to a hemodynamic variable of said patient over a period of time, means for encoding said first data into a plurality of first digitally coded signals, means for transmitting said first digitally coded signals to said computer, a monitor in electronic communication with said computer for visually displaying information relating to said first data, and a keyboard in electronic communication with said computer for providing bedside control of said system, comprising:

(a) repeating steps (b) through (1) at the end of successive periods, of time, wherein said time period is a preselected period of time, until a predetermined interval of time has elapsed;

(b) storing the value for said hemodynamic variable in the memory of said computer;

(c) determining if said infusion pump is in an alarm state;

(d) ascertaining the incremental volume of said blood pumped through said first infusion pump during said preselected period of time;

(e) calculating the total volume of said blood infused by summing the respective said ascertained incremental volumes;

(f) computing the volume of said blood in said chamber;

(g) calculating the volume difference in said chamber between said computed volume in said chamber and the volume of said blood in said chamber after the previous said preselected period of time;

(h) computing the incremental volume of blood drainage from the mediastinum during said preselected period to time by summing said volume difference and said ascertained volume of blood pumped through said first infusion pump;

(i) calculating the total amount of blood drainage from the mediastinum by summing said computed incremental volumes over a predetermined interval of time;

(j) setting said first infusion rate at a predetermined low rate to keep said patient's vein open upon the occurrence of a selected one of the following conditions:

(i) if the volume of said blood in said chamber is less than a predetermined acceptable volume;

(ii) if said value for said hemodynamic variable does not fall within a predetermined acceptable range;

(iii) if said volume of blood drainage from the mediastinum during said preselected period of time exceeds a predetermined acceptable value;

(k) setting said first infusion rate to deliver an aliquot of said blood at a predetermined acceptable rate unless said predetermined low rate was set in step (j); and (l) allowing the infusion of said blood at said first infusion rate unless said first pump is in said alarm state.

25. The method of claim 24 to further provide for infusing of circulatory supportive fluids by means of a second infusion pump having a second variable infusion rate that is controlled by said computer, a reservoir containing a biocompatible fluid, fourth conduit means for transferring said biocompatible fluid from said reservoir to said second infusion pump, fifth conduit means for transferring said biocompatible fluid from said second infusion pump into the vein of said patient, means for collecting second data relating to a physiological variable of said patient over a period of time, means for encoding said second data into a plurality of second digitally coded signals, and means for transmitting said second digitally coded signals to said computer, comprising analyzing in said computer said second digitally coded signals to set said rate of said second infusion pump for a preselected period of time.

26. The method of claim 25, wherein said biocompatible fluid is washed autologous blood.

27. The method of claim 24, wherein said first infusion pump is a volumetric infusion pump.

28. The method of claim 24, wherein said blood collection chamber is a cardiotomy reservoir.

29. The method of claim 24, wherein said hemodynamic variable is the right atrial pressure.

30. The method of claim 24, wherein said hemodynamic variable is the left atrial pressure.

31. The method of claim 24, wherein said first data provides the volume of said blood in said chamber at a particular time.

32. The method of claim 24, wherein said first data provides the volume of said blood pumped through said first infusion pump during said preselected period of time.

33. The method of claim 24, wherein said first rate of said first infusion pump is set by said computer through a point-to-point topology pump addressing scheme.

34. The method of claim 24, wherein said first infusion pump infuses a volume of said blood followed by a period of time during which said blood is not infused by said first infusion pump to allow the collecting of said first data without infusion-related distortion during said period of time.

35. The method of claim 24, wherein said preselected period of time is one minute.

* * * * *